United States Patent
Kim et al.

(10) Patent No.: US 6,639,069 B2
(45) Date of Patent: Oct. 28, 2003

(54) METHOD OF PREPARING AND USES OF CUCURBITURIL DEVICES

(75) Inventors: Kimoon Kim, Pohang (KR); Jaheon Kim, Pohang (KR); In-Sun Jung, Pohang (KR); Soo-Young Kim, Pohang (KR); Eunsung Lee, Pohang (KR); Jin-Koo Kang, Pohang (KR)

(73) Assignee: Pohang University of Science and Technology, Pohang (KR)

( * ) Notice: Subject to any disclaimer, the term of this patent is extended or adjusted under 35 U.S.C. 154(b) by 0 days.

(21) Appl. No.: 10/092,468

(22) Filed: Mar. 8, 2002

(65) Prior Publication Data

US 2002/0133003 A1 Sep. 19, 2002

Related U.S. Application Data

(62) Division of application No. 09/605,635, filed on Jun. 28, 2000, now Pat. No. 6,365,734.

(30) Foreign Application Priority Data

Oct. 21, 1999 (KR) ......................................... 1999-45842
Jun. 15, 2000 (KR) ......................................... 2000-33026

(51) Int. Cl.$^7$ ..................... C07D 245/04; C07D 487/04
(52) U.S. Cl. ..................................................... 540/460
(58) Field of Search ......................................... 540/460

(56) References Cited

FOREIGN PATENT DOCUMENTS

DE 19603377 * 8/1997
WO WO 00/68232 11/2000

OTHER PUBLICATIONS

Kim et al., J. Am. Chem. Soc., Jan. 26, 2000, vol. 122, Issue 3, pp. 540–541.*
Flinn et al., Angew. Chem. Int. Ed. Engl., 1992, vol. 31, No. 11, pp. 1475–1477.*
Buschmann et al., CA 127:205599, 1997.*

* cited by examiner

*Primary Examiner*—Laura L. Stockton
(74) *Attorney, Agent, or Firm*—Leydig, Voit & Mayer, Ltd.

(57) ABSTRACT

Cucurbituril derivatives, their preparation methods and uses. The cucurbituril derivatives have the formula (1)

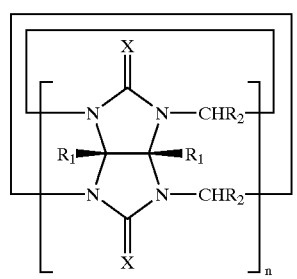

(1)

where X is O, S or NH; $R_1$ and $R_2$ are independently selected from the group consisting of hydrogen, alkyl groups of 1 to 30 carbon atoms, alkenyl groups of 1 to 30 carbon atoms, alkynyl groups of 1 to 30 carbon atoms, alkylthio groups of 1 to 30 carbon atoms, alkylcarboxyl groups of 1 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n is an integer from 4 to 20, wherein the cucurbituril derivatives having the formula (1), where n=6, $R_1$=H, $R_2$=H and X=O, and n=5, $R_1$=CH$_3$, $R_2$=H and X=O, are excluded. The cucurbituril derivatives are easily prepared as a mixture by one of the three new methods, and each cucurbituril derivative can be separated from the mixture by fractional crystallization. The cucurbituril derivatives having the formula (1) or their mixtures are very useful in removing dyes and heavy metal ions dissolved in water or waste water.

19 Claims, 3 Drawing Sheets

METHOD OF PREPARING AND USES OF CUCURBITURIL DEVICES

This is a divisional of application Ser. No. 09/605,635, filed Jun. 28, 2000, now U.S. Pat. No. 6,365,734 the disclosure of which is incorporated by reference.

BACKGROUND OF THE INVENTION

1. Field of the Invention

The present invention is directed to the composition, methods of preparation and uses novel cucurbituril derivatives having various repeating units and cavities of various sizes.

2. Description of the Related Art

Cucurbituril is a macrocyclic compound whose preparation was first reported by Behrend et al. in 1905 (*Liebigs Ann. Chem.* 1905, 339, 1). According to their report, the condensation of glycoluril and excess formaldehyde in the presence of hydrochloric acid (HCl) produces an amorphous solid. Dissolution of the solid in hot concentrated sulfuric acid, dilution of the solution with water followed by slow cooling of the solution to room temperature produces a crystalline material. They wrongly characterized this substance as $C_{10}H_{11}N_7O_4 \cdot 2H_2O$ solely based on elemental analysis. In 1981, this substance was rediscovered by Mock and coworkers (*J. Am. Chem. Soc.,* 1981, 103, 7367). They correctly characterized it as a hexameric macrocyclic compound with composition of $C_{36}H_{36}N_{24}O_{12}$, which was also confirmed by X-ray crystal structure determination. They named it cucurbituril which we from now on refer to as cucurbit[6]uril.

Since then an improved preparation procedure for cucurbit[6]uril has been disclosed (DE 196 03 377 A1). According to this new procedure, in the presence of an acid, glycoluril and formaldehyde are reacted at 100° C. or a higher temperature, and then the reaction mixture is further heated up to 150° C. to concentrate the reaction mixture. Cooling the mixture to room temperature results in cucurbit [6]uril. This synthetic method can increase the yield of cucurbit[6]uril. However, it was reported to produce only the hexameric cucurbituril, cucurbit[6]uril, with improved yield. The cucurbituril derivatives having less or more than six monomers cannot be synthesized by the method. Moreover, the synthetic method requires a much higher reaction temperature, which makes it less practical.

In addition, decamethylcucurbit[5]uril, in which five dimethanodimethylglycoluril units form a cyclic structure by the condensation of dimethylglycoluril and formaldehyde, has been reported (*Angew. Chem. Int. Ed. Engl.* 1992, 31, 1475).

As described above, up to now, only two cucurbituril derivatives, cucurbit[n]uril with n=6 and decamethyl-cucurbit[n]uril with n=5, have been reported. The known cucurbituril derivatives are very limited in terms of types and cavity sizes (5.5 or less). Also, they are insoluble in common solvents such as water or methanol, and thus their applications are limited.

SUMMARY OF THE INVENTION

The first objective of the present invention is to provide novel cucurbituril derivatives with various-sized cavities and/or with enhanced solubilities in common solvents.

The second objective of the present invention is to provide easy preparation methods for the cucurbituril derivatives.

The third objective of the present invention is to provide the uses of the cucurbituril derivatives.

The first objective of the present invention is achieved by cucurbituril derivatives having the formula (1)

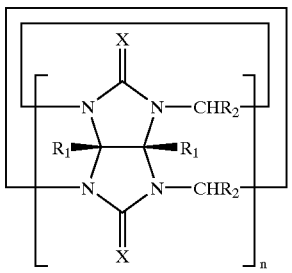

(1)

where X is O, S or NH; $R_1$ and $R_2$ are independently selected from the group consisting of hydrogen, alkyl groups of 1 to 30 carbon atoms, alkenyl groups of 2 to 30 carbon atoms, alkynyl groups of 2 to 30 carbon atoms, alkylthio groups of 1 to 30 carbon atoms, alkylcarboxyl groups of 2 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n is an integer from 4 to 20, wherein the cucurbituril derivatives having the formula (1), where n=6, $R_1$=H, $R_2$=H and X=O, and n=5, $R_1$=$CH_3$, $R_2$=H and X=O, are excluded.

The second objective of the present invention is achieved by new preparation methods for cucurbituril derivatives having the formula (1)

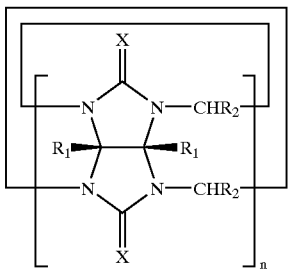

(1)

where X is O, S or NH; $R_1$ and $R_2$ are independently selected from the group consisting of hydrogen, alkyl groups of 1 to 30 carbon atoms, alkenyl groups of 2 to 30 carbon atoms, alkynyl groups of 2 to 30 carbon atoms, alkylthio groups of 1 to 30 carbon atoms, alkylcarboxyl groups of 2 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n is an integer from 4 to 20.

The basic process of the invention used for the preparation of cucurbituril derivatives having formula (1) hereinabove comprises: (a1) adding 3 to 7 moles of an acid to 1 mole of compound (A) hereinbelow to form a mixture, adding 2 to 20 moles of alkylaldehyde (B) hereinbelow to the mixture, and stirring the mixture at 70 to 95° C.; and (b1) stirring the reaction mixture at 95 to 105° C. to complete the reaction.

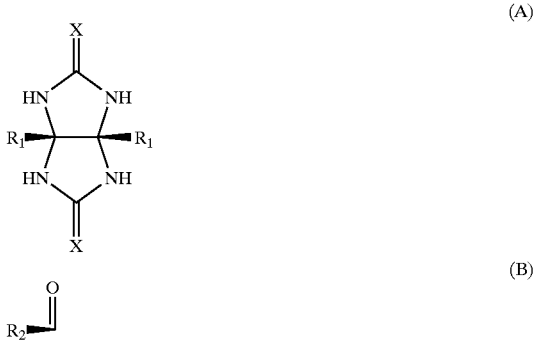

In another embodiment, the cucurbituril derivatives having formula (1) hereinabove may be formed by (a2) adding 0.1 to 1 moles of an acid to 1 mole of compound (A) hereinabove to form a mixture, adding 2 to 20 moles of alkylaldehyde (B) hereinabove to the mixture, and stirring the mixture at 70 to 85° C., to obtain an intermediate in a gel state; and (b2) drying the gel, adding 3 to 7 moles of an acid for each mole of the dried intermediate, and stirring the reaction mixture at 70 to 105° C.

In still another embodiment, the cucurbituril derivatives having the formula (1) hereinabove may be formed by (a3) placing compound (A) hereinabove, and 0.1 to 1 moles of an acid and 2 to 20 moles of alkylaldehyde(B) hereinabove for each mole of compound (A) hereinabove, in a high-pressure reactor, and reacting the mixture at 80 to 130° C. to obtain an oligomeric intermediate in powder form; and (b3) adding 3 to 7 moles of an acid for each mole of the oligomeric intermediate, and stirring the mixture at 70 to 105° C.

The reaction products of steps (b1), (b2) and (b3) are a mixture of two or more cucurbituril derivatives having the formula (2) with n of a value from 5 to 20, depending on the reaction conditions.

The typical reaction products of steps (b1), (b2) and (b3) are a mixture of 5–30% of the cucurbituril derivative having n=5, 30–70% of the cucurbituril derivative having n=6, 5–30% of the cucurbituril derivative having n=7, 2–15% of the cucurbituril derivative having n=8, and 1–10% of the cucurbituril derivative having n=9 through 20.

Each of the above three methods for preparing cucurbituril derivatives having the formula (1) hereinabove, may further comprise: (c1) crystallizing the cucurbituril derivative having the formula (1) with n=8 from the product mixtures obtained in step (b1), (b2) or (b3); (d1) diluting the remaining solution after step (c1) with water and acetone to produce a precipitate which is filtered and further treated in step (e1), and removing the solvent from the resulting filtrate to obtain the cucurbituril derivatives having the formula (1), with n ranging from 9 to 20; and (e1) partially dissolving the precipitate obtained in step (d1) in water to obtain the cucurbituril derivatives with n=5 and 7 from the water soluble fraction, and the cucurbituril derivative with n=6 from the water insoluble fraction. Separation of the cucurbituril derivative with n=5 from the cucurbituril derivative with n=7 in the water soluble fraction, which is obtained from step (e1), is achieved by partial precipitation using a mixed solvent of water and methanol.

In another aspect of the present invention, the cucurbituril derivatives having the formula (1) prepared by the inventive methods can be utilized to remove organic dyes from waste water, heavy metal from water, and radioactive isotopes from radioactive wastes, to capture and remove unpleasant odor, and air pollutants such as carbon monoxide, carbon dioxide, $NO_x$ and $SO_x$, and to deodorize and decolorize livestock waste water and ironwork waste water. Also, the cucurbituril derivatives having the formula (1) are applicable in manufacturing sensors for sensing ammonium ions, organic amines, amino acid derivatives, nucleic acid bases, alkali metal or alkaline earth metal ions. The cucurbituril derivatives having the formula (1) can be used as additives to polymers, cosmetics, artificially scented papers or textiles, pesticides and herbicides, and drugs, and used as drug carriers. The cucurbituril derivatives having the formula (1) can be used for extraction and purification of fullerene or caborane compounds, and used as packing materials of chromatographic columns, as additives to gas separation membranes, as catalysts for various chemical reactions.

For such applications, any cucurbituril derivative synthesized in the present invention can be used. A mixture of the cucurbituril derivatives from step (b1), (b2) or (b3) can be used for the above-listed purposes without further purification.

BRIEF DESCRIPTION OF THE DRAWINGS

The above objectives and advantages of the present invention will become more apparent by describing in detail preferred embodiments thereof with reference to the attached drawings in which.

DETAILED DESCRIPTION OF THE INVENTION

Figure 1:
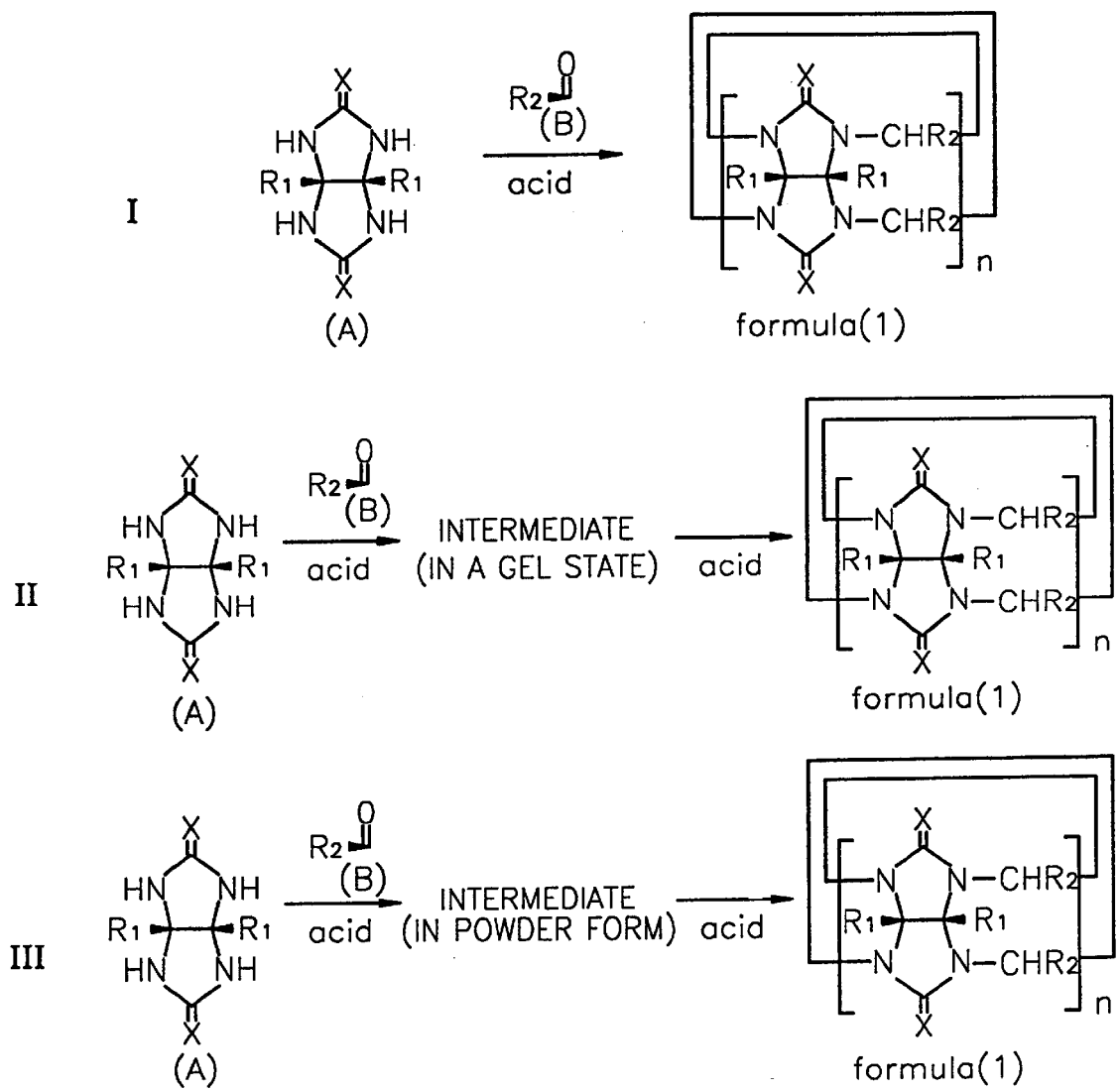
FIG. 1 is a diagram illustrating the synthetic pathways of cucurbituril derivatives according to the present invention.

The present invention provides the cucurbituril derivatives having the formula (1)

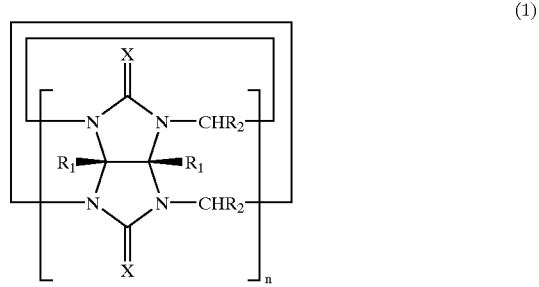

where X is O, S or NH; $R_1$ and $R_2$ are independently selected from the group consisting of hydrogen, alkyl groups of 1 to 30 carbon atoms, alkenyl groups of 2 to 30 carbon atoms, alkynyl groups of 2 to 30 carbon atoms, alkylthio groups of 1 to 30 carbon atoms, alkylcarboxyl groups of 2 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n is an integer from 4 to 20, wherein the cucurbituril derivatives The alkyl groups of 1 to 30 carbon atoms for $R_1$ and $R_2$ may include methyl, ethyl, propyl, isopropyl and t-butyl groups. The alkenyl groups of 2 to 30 carbon atoms for $R_1$ and $R_2$ may include propylene and butene groups, and the alkynyl groups of 2 to 30 carbon atoms therefor may include a hexynyl group. The alkylthio groups of 1 to 30 carbon atoms may include butylmethylsulfide and octanethiol groups. The alkylcarboxyl groups of 2 to 30 carbon atoms may include carboxypropyl and carboxylbutyl groups, and the hydroxyalkyl groups of 1 to 30 carbon atoms may include hydroxybutyl and hydroxyethyl groups. The alkylsilyl groups of 1 to 30 carbon atoms may include aryltriethylsilyl and vinyltriethylsilyl groups, and the alkoxy groups of 1 to 30 carbon atoms may include methoxy and ethoxy groups. The haloalkyl groups of 1 to 30 carbon atoms may include $CF_3$ and $CH_2Cl$, and the aminoalkyl groups of 1 to 30 carbon atoms may include 2-aminobutyl and 1-aminobutyl groups. The unsubstituted cycloalkyl groups of 5 to 30 carbon atoms may include cyclohexyl and cyclopentyl groups, and the cycloalkyl groups of 4 to 30 carbon atoms with hetero atoms may include piperidyl and tetrahydrofuranyl groups. The unsubstituted aryl groups of 6 to 30 carbon atoms may include phenyl, benzyl and naphthyl groups, and the aryl groups of 6 to 30 carbon atoms with hetero atoms may include pentafluorophenyl and pyridyl groups.

In consideration of the above examples of $R_1$ and $R_2$ in the formula (1) hereinabove, the following compounds may be examples of the cucurbituril derivatives having the formula (1).

In other words, in the formula (1) hereinabove, $R_1$ may be methyl, ethyl, propyl, isopropyl, butyl, isobutyl, t-butyl, phenyl or pyridyl group, and $R_2$ may be hydrogen, methyl, propyl, phenyl, trichloromethyl, trifluoromethyl, parafluorophenyl or α,α,α-trifluorotolyl group. Alternatively, $R_1$ may be hydrogen, and $R_2$ may be methyl, ethyl, propyl, phenyl, trichloromethyl, trifluoromethyl, parafluorophenyl or α, α,α-trifluorotolyl group. In another embodiment, $R_1$ may be methyl group, and $R_2$ may be methyl, ethyl, propyl, phenyl, trichloromethyl, trifluoromethyl, parafluorophenyl or α,α,α-trifluorotolyl group. More preferable cucurbituril derivatives have the formula (1) hereinabove, wherein X=O, $R_1$ and $R_2$ are both hydrogens, and n=5, or a value of 7 to 20, and wherein X=NH or S, $R_1$ and $R_2$ are both hydrogens, and n is a value of 5 to 20.

Hereinafter, the methods for synthesizing the cucurbituril derivatives according to the present invention will be described. The following methods, which are different from their conventional synthetic methods, can also be applied to the synthesis of the cucurbituril derivatives having the formula (1) with n=6, $R_1$=H, $R_2$=H and X=O, or with n=5, $R_1$=$CH_3$, $R_2$=H and X=O, which are already known.

The method for synthesizing the cucurbituril derivatives according to the present invention can be classified into one of three methods, according to the reaction conditions and the state of intermediate products (refer to FIG. 1).

As for the first synthesis method of cucurbituril derivatives, an acid is added to compound (A) in an amount of 3 to 7 moles with respect to 1 mole of compound (A), and mixed. Preferably, the acid is diluted with water or an organic solvent to be 1 to 12M, but preferably to be 6 to 12M. Any acid capable of dissolving compound (A) such as glycoluril ($R_1$=H), for example, hydrochloric acid, sulfuric acid, phosphoric acid, acetic acid, nitric acid and an mixtures of these acids, can be used. The organic solvent as an acid diluent may be dimethylsulfoxide, N,N-dimethylformamide, methanol, ethanol, chloroform or an mixture of these solvents.

Compound (A) (X=O) can be synthesized by the following method, and compound (A) with $R_1$=H and X=O (glycoluril) can be purchased.

As shown in the following reaction scheme, urea and compound (C) are dissolved in an aqueous acidic solution or an acid-containing organic solvent, and stirred for a certain period of time. Removal of water or the organic solvent from the reaction mixture produces compound (A) (X=O). The compound (A) with X=S or NH can be obtained by a similar procedure.

(Reaction Scheme)

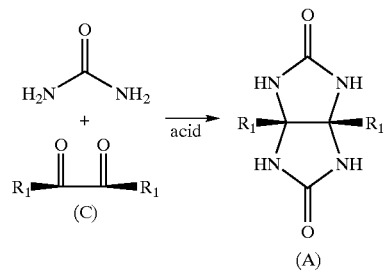

Compound A (X=O) is reacted with alkylaldehyde (B) in an acidic solution while stirring at 70 to 95° C. for 6 to 24 hours. The amount of alkylaldehyde (B) used is 2 to 20 moles for each mole of glycoluril, but preferably, 4 moles. For example, alkylaldehyde (B) may be formaldehyde, acetaldehyde, propionaldehyde, benzaldehyde, and the like. During the reaction, the color of the reaction solution changes into dark red with time.

The reaction mixture is subjected to a further reaction at 95 to 105° C. The final reaction product varies depending on the reaction temperature and the amount of reactants. The usual final reaction product is a mixture of two or more cucurbituril derivatives having the formula (1) hereinabove, where n is a value from 5 to 20.

Typically, the reaction product is a mixture of 5 to 30% of the cucurbituril derivative with n=5, 30 to 70% of the cucurbituril derivative with n=6, 5 to 30% of the cucurbituril derivative with n=7, 2 to 15% of the cucurbituril derivative with n=8, and 1 to 10% of the cucurbituril derivatives with n=9 to 20.

However, during the reaction at 95 to 105° C., the cucurbituril derivative with n=6 may precipitate in a crystalline form, depending on the reaction temperature, moisture content in the air, and concentration of reactants.

Figure 2:
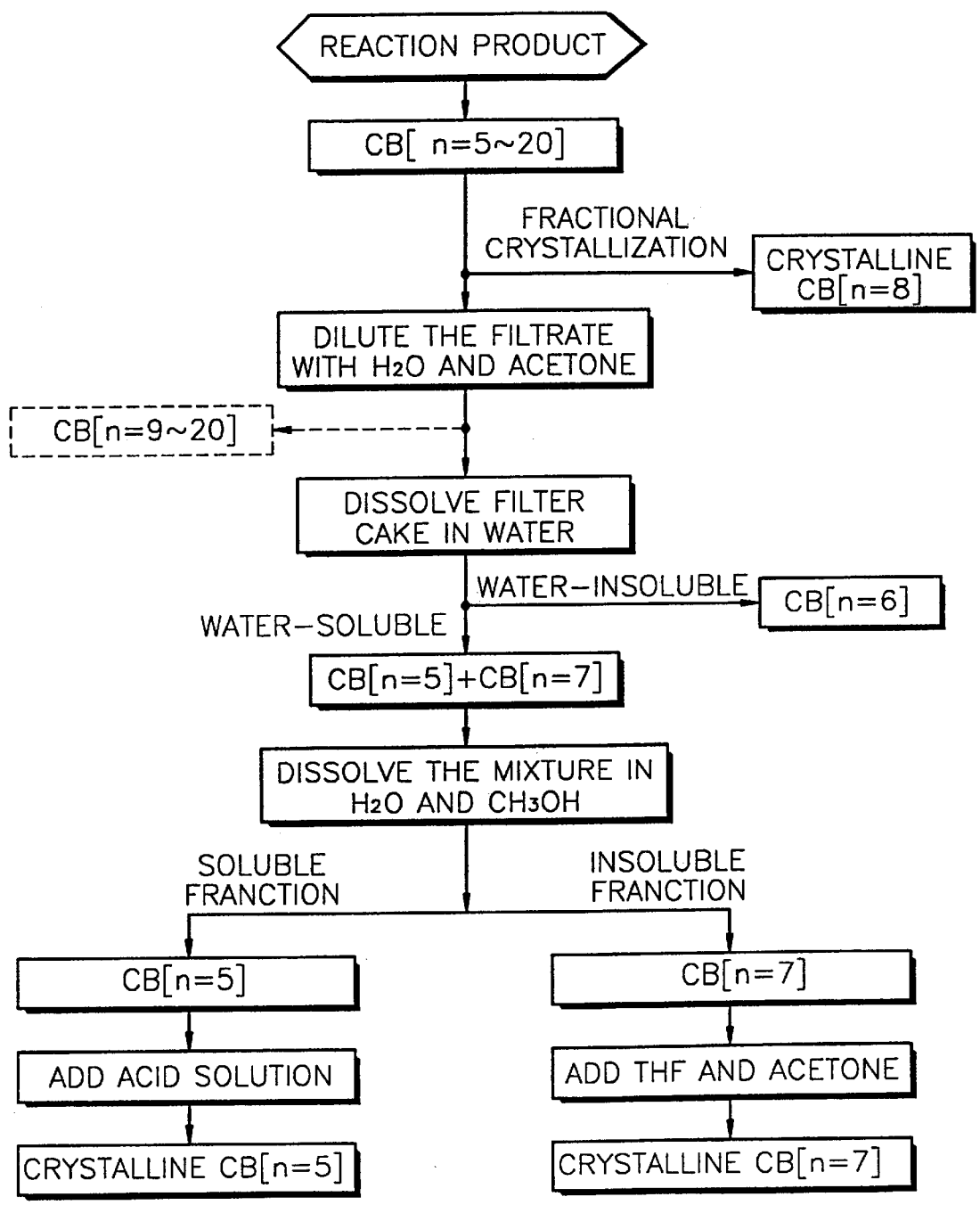
FIG. 2 illustrates the separation of the cucurbituril derivatives obtained through the pathways illustrated in FIG. 1.

Then, the resulting cucurbituril derivatives are separated from each other by the following fractional crystallization procedure shown in FIG. 2.

First, the final reaction mixture is diluted with water and left on bench at room temperature to give the cucurbituril derivative having the formula (1) hereinbelow, where n=8.

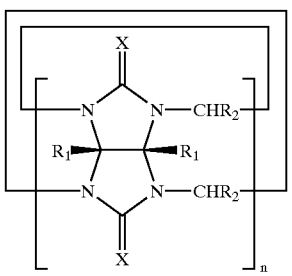

(1)

where X is O, S or NH; $R_1$ and $R_2$ are independently selected from the group consisting of hydrogen, alkyl groups of 1 to 30 carbon atoms, alkenyl groups of 2 to 30 carbon atoms, alkynyl groups of 2 to 30 carbon atoms, alkylthio groups of 1 to 30 carbon atoms, alkylcarboxyl groups of 2 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n is an integer from 4 to 20.

During this separation step, the cucurbituril derivative with n=6 may be formed in crystalline form, and can be easily separated from the cucurbituril derivative with n=8 in the formula (1), with a solvent. The solvent for use in the separation of the cucurbituril derivative with n=6 may be an alkali metal ion salt solution, such as $Na_2SO_4$ or $K_2SO_4$, an amine-acid salt solution ($H_2N—R—NH_2 \cdot 2HCl$) or a formic acid solution. The crystalline cucurbituril derivative with n=6 is soluble in such a solvent, whereas the cucurbituril derivative with n=8 is relatively less soluble in the solvent, which enables the separation of the two reaction products.

After separation of the cucurbituril derivative with n=8 in the formula (1), the filtrate is further diluted with water and acetone, and filtered. Preferably, water and acetone are added in a ratio of 1:3 to 1:7 by volume. The filtrate after the filtration contains the cucurbituril derivatives having the formula (1), where n=9 to 20. Meanwhile, the filter cake is dissolved in water. Here, the cucurbituril derivatives with n=5 and 7 in the formula (1) are obtained as a major component of the water soluble fraction. The major component in the water insoluble fraction is the cucurbituril derivative with n=6 in the formula (1).

The cucurbituril derivatives with n=5 and 7 in the formula (1) can be separated from each other, as illustrated in FIG. 2, with a mixture of water and methanol in a ratio of 1:0.7 to 1:1.3 by volume. That is, water and methanol are added to the solution containing both the cucurbituril derivatives with n=5 and 7, and filtered. The insoluble fraction is then recrystallized with tetrahydrofuran (THF) and acetone to obtain the pure crystalline cucurbituril derivative with n=7 in the formula (1). Also, the filtrate, which is the water and methanol soluble fraction, is recrystallized with an aqueous solution of acid to obtain the crystalline cucurbituril derivative with n=5 in the formula (1).

In the second synthetic method of the cucurbituril derivatives according to the present invention, a relatively small amount of acid than in the previously mentioned method is added to the reaction mixture of compound (A) and alkylaldehyde (B) to result in an intermediate product in a gel state. Then, the intermediate product is treated with an acid to obtain the cucurbituril derivatives having the formula (1) hereinabove.

In particular, an acid is added to compound (A) in an amount of 0.1 to 1 moles with respect to 1 mole of compound (A). The acid added may be diluted with water or an organic solvent in the same ratio as in the first method mentioned above. Examples of the useful organic solvents have been described in the first synthesis method, and thus examples of the organic solvents are not listed herein.

Then, 2 to 20 moles, but preferably, 2 to 4 moles, of alkylaldehyde (B) with respect to 1 mole of compound (A) is added to the mixture, and reacted at 70 to 85° C. to obtain the intermediate product in a gel state.

After drying the intermediate product, 3 to 7 moles of an acid with respect to 1 mole of the intermediate product are added and stirred at 70 to 105° C. Here, the acid is diluted with water or an organic solvent prior to the addition.

In the present method, the final reaction product slightly varies depending on the reaction temperature and the amount of reactants, as in the first synthesis method. However, the usual final reaction product is a mixture of two or more cucurbituril derivatives in the formula (1) hereinabove, where n is a value from 5 to 20.

Typically, the final reaction product is a mixture of 5 to 30% of the cucurbituril derivative having n=5, 30 to 70% of the cucurbituril derivative having n=6, 5 to 30% of the cucurbituril derivative having n=7, 2 to 15% of the cucurbituril derivative having n=8, and 1 to 10% of the cucurbituril derivatives having n=9 to 20.

Then, the fractional separation described with reference to FIG. 2 is carried out to give the cucurbituril derivatives having the formula (2) hereinabove, where n is a value from 5 to 20, as in the first synthesis method.

The third synthetic method of the cucurbituril derivatives disclosed by the present invention involves a reaction under a high pressure condition, which is different from the two previously mentioned synthetic methods. In this synthetic method, the amount of acid added for the reaction with compound (A) and alkylaldehyde(B) is reduced, as in the second synthesis method, to produce oligomer powder as an intermediate product. The obtained intermediate product is treated with an acid to synthesize the cucurbituril derivatives having the formula (1) hereinabove. In contrast to the two previously mentioned methods, the cucurbituril derivative having n=7 is produced in a relatively higher yield, whereas the cucurbituril derivative having n=6 is produced in a relatively lower yield.

In particular, compound (A), an acid and alkylaldehyde (B) are put into a high-pressure reactor. Here, 0.1 to 1 moles of acid and 2 to 4 moles of alkylaldehyde(B) are added with respect to 1 mole of compound (A). The acid is diluted with water or an organic solvent prior to use. The concentration of the diluted acid solution may vary depending on the reaction conditions, but preferably, 1 to 12M, more preferably 6 to 12M, of the acid solution is added. Then, the mixture is reacted at 80 to 130° C. Preferably, the reaction is carried out under a pressure of 15 to 100 psi, but preferably, 20 to 80 psi. If the reaction pressure is higher than 100 psi, it may place the synthesis process itself into a dangerous situation. Meanwhile, if the reaction pressure is lower than 15 psi, the yield may be low.

After the reaction is completed, the solid reaction product is washed with water or an organic solvent and dried to yield oligomers in powder form as an intermediate product.

Then, 3 to 7 moles of an acid for each mole of oligomers is added to the oligomers, and the mixture is stirred at 70 to 105° C. The acid added herein is diluted with water or an organic solvent, as in the first and second synthesis methods. The concentration and types of the useful acids are also identical to those in the first and second synthesis methods. As a result, a mixture of two or more cucurbituril derivatives having the formula (2), where n is a value from 5 to 20, is obtained as in the first and second synthesis methods.

Typically, the final reaction product is a mixture of 5 to 30% of the cucurbituril derivative having n=5, 30 to 70% of the cucurbituril derivative having n=6, 5 to 30% of the cucurbituril derivative having n=7, 2 to 15% of the cucurbituril derivative having n=8, and 1 to 10% of the cucurbituril derivatives having n=9 to 20.

After the reaction between the oligomers and the acid is completed, the separation procedure shown in FIG. 2 is carried out to give the cucurbituril derivatives having the formula (1) hereinabove, where n is a value from 5 to 20, as in the first and second synthesis methods.

The cucurbituril derivatives having the formula (1) with X=S can also be synthesized by the above-described methods using compound (A) with X=S, instead of with X=O. Here, compound (A) with X=S can be synthesized in the same way described previously, except that thiourea instead of urea is used. Furthermore, the above-described methods can be applied in synthesizing the cucurbituril derivatives having the formula (1) with X=NH.

The present invention provides easy preparation methods for the cucurbituril derivatives having the formula (1), where n ranges from 5 to 20, and separation methods based on their different solubilities in a common solvent such as water, acetone and methanol.

The cucurbituril derivatives having the formula (1) disclosed by the present invention, which can be used as a substitute for cyclodextrine, have cavities having a diameter of 4 to 15 Å, which are able to include guest molecules, such as cyclic benzene derivatives, naphthalene derivatives, carborane derivatives, fullerene derivatives, ferrocene derivatives and adamantane derivatives in their cavities. The cucurbituril derivatives can selectively remove such compounds by the inclusion therein. In the case where X=O in the formula (1) and the cucurbituril derivatives are complexed with an ammonium salt or an alkali metal ion, the cucurbituril derivatives are soluble in water. Also, the cucurbituril derivatives coprecipitate with organic dyes at a certain pH. In the case when X is S or NH, or $R_1$ or $R_2$ is propyl or longer alkyl chain, the cucurbituril derivatives are soluble in organic solvents, providing wider applications than previously known cucurbituril derivatives.

The cucurbituril derivatives having the formula (1) can include various compounds with different sizes, and have Lewis base atoms near the cavities of the molecule, which can form chemical bonds with charged metal ions, organometallic ions or organic compounds, and thus the cucurbituril derivatives can have a wide range of applications. In particular, the cucurbituril derivatives having the formula (1) according to the present invention can be used to remove organic dyes from waste water, heavy metal from water, and radioactive isotopes from radioactive wastes, to capture and remove unpleasant odor, and air pollutants such as carbon monoxide, carbon dioxide, NOx and SOx, and to deodorize and decolorize livestock waste water and ironwork waste water. Also, the cucurbituril derivatives having the formula (1) are applicable in manufacturing sensors for sensing ammonium ions, organic amines, amino acid derivatives, nucleic acid bases, alkali metal or alkaline earth metal ions. The cucurbituril derivatives having the formula (1) can be used as additives to polymers, cosmetics, artificially scented papers or textiles, pesticides and herbicides, and drugs, and used as drug carriers. The cucurbituril derivatives having the formula (1) can be used for extraction and purification of fullerene or caborane compounds, and used as packing materials of chromatographic columns, as additives to gas separation membranes, as catalysts for various chemical reactions.

For the above listed purposes, the cucurbituril derivatives may be used in mixed form along with the cucurbituril derivative having the formula (1), wherein n=6, $R_1$=H, $R_2$=H and X=O, and/or the cucurbituril derivative having the formula (1), wherein n=5, $R_1$=CH$_3$, $R_2$=H and X=O.

In the applications of the cucurbituril derivatives disclosed by the present invention, a certain pure cucurbituril derivative or a mixture of cucurbituril derivatives can be used. However, if the difference in effect is not great among types of the cucurbituril derivatives used, use of the mixture of cucurbituril derivatives prepared by one of the three methods in FIG. 1 is preferred in terms of cost, because it does not need additional separation process.

The present invention will be described in greater detail by means of the following examples. The following examples are for illustrative purposes and not intended to limit the scope of the invention.

Synthesis Example 1

Preparation of the Cucurbituril Derivative Having the Formula (1) where n=5, X=O, $R_1$=H and $R_2$=H Method 1

5.68 g of glycoluril was added to 20 ml of 9M-hydrosulfuric acid ($H_2SO_4$) aqueous solution and stirred at 70° C. 7.0 ml of formaldehyde was added to the reaction mixture and stirred at 70 to 75° C. for 24 hours.

Then, the temperature of the reaction mixture was further raised up to 95 to 100° C. and stirred for 12 hours. The reaction product was diluted with 50 ml of water and 1.0 l of acetone was added to form a precipitate. The obtained precipitate was filtered, washed with acetone and dried for 24 hours.

The precipitate was dissolved in 200 ml of water, and the water insoluble fraction was filtered away. 800 ml of acetone was added to the filtrate for reprecipitation. The precipitate was filtered and dissolved in 200 ml of water and methanol mixture (mixed in a ratio of 1:1 by volume). The insoluble fraction in the water and methanol mixture was filtered away and 100 ml of acetone was added to the filtrate to form a precipitate.

The precipitate was filtered, washed with acetone and vacuum dried for 24 hours. The dried powder was dissolved in 1 M-$H_2SO_4$ solution and stored at 5 to 10° C. to give a colorless crystalline cucurtbit[5]uril in a yield of 10%.

Method 2

8 ml of formaldehyde was added to 5.68 g of glycoluril and stirred at 75° C. for 20 minutes. 1 ml of 12M-HCl aqueous solution was added to the reaction mixture and stirred at 70 to 75° C. for 30 minutes. After the reaction was completed, the reaction solution hardened, forming a gel. The obtained gel was washed with water and acetone, and vacuum dried overnight.

18 ml of 11M-$H_2SO_4$ aqueous solution was added to the resultant solid compound and stirred at 80° C. for 12 hours.

The reaction mixture was diluted with 200 ml of water, and 1.0 l of acetone was further added to form a precipitate. The precipitate was filtered and then stirred in a mixture of 200 ml of water and 800 ml of acetone for 5 minutes. The precipitate was filtered and dissolved in 200 ml of water. Then, the water insoluble fraction was filtered and 1.0 l of acetone was added to the filtrate to form a precipitate. The precipitate was filtered and dissolved in a mixture of 50 ml of water and 60 ml of methanol. The insoluble fraction was filtered and 500 ml of acetone was added to the filtrate to form a precipitate. The precipitate was filtered, washed with acetone, and dried for 24 hours to give a cucurbit[5]uril in a yield of 10%.

Method 3

5.68 g of glycoluril, 10.0 ml of formaldehyde and 1.0 ml of concentrated HCl were put into a high-pressure reactor, and reacted at 115° C. for 12 hours. After the reaction was completed, a powdered reaction product was obtained. The powdered reaction product was washed with water and acetone, and vacuum dried overnight. 10 ml of 10M-$H_2SO_4$ aqueous solution was added to the dried compound, and stirred at 80° C. for 12 hours.

The reaction product was diluted with 200 ml of water, and 1.0 l of acetone was added to the solution to form a precipitate. The precipitate was filtered, washed with acetone and vacuum dried for 25 hours.

The precipitate was dissolved in 200 ml of water and 600 ml of acetone, and filtered. The obtained precipitate was dissolved in 150 ml of water and filtered. 1.0 l of acetone was added to the filtrate to form a precipitate. The precipitate was filtered and dissolved in a mixture of 50 ml of water and 60 ml of methanol. The insoluble fraction in the water and methanol solution was filtered away and 500 ml of acetone was added to the filtrate to form a precipitate.

The precipitate was filtered, washed with acetone, and vacuum dried to give white solid cucurbit[5]uril in a yield of 10%.

$^1$H NMR ($D_2O/CF_3COOD/D_2SO_4$, 500 MHz), δ4.43 (d, 10H, J=15.5 Hz), 5.65 (s, 10H), 5.85 (d, 10H, J=15.5 Hz)

$^{13}$C NMR ($D_2O/CF_3COOD/D_2SO_4$, 125 MHz), δ54.0, 72.9, 160.0

Figure 3:
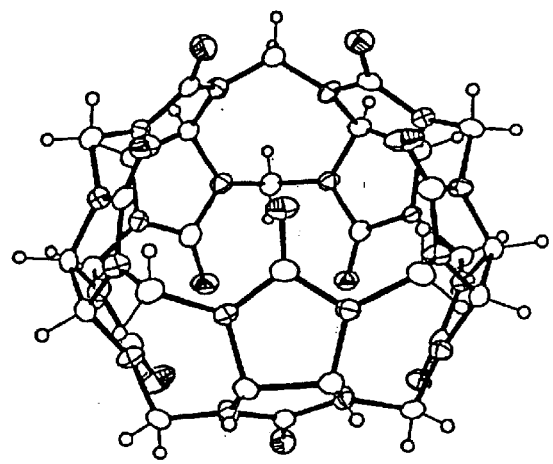
FIGS. 3 through 5 show the X-ray crystal structures of the cucurbituril derivatives prepared in Synthesis Examples 1 through 3, respectively.

The crystal structure of the obtained cucurbituril derivative was determined by X-ray crystallography. The result is shown in FIG. 3.

Synthesis Example 2

Preparation of the Cucurbituril Derivative Having the Formula (1) where n=7, X=O, $R_1$=H and $R_2$=H Method 1

5.68 g of glycoluril was added to 20 ml of 9M-$H_2SO_4$ aqueous solution and stirred at 70° C. for 30 minutes. 7.0 ml of formaldehyde was added to the reaction mixture and stirred at 75° C. for 24 hours.

Then, the reaction mixture was diluted with 200 ml of water, and 1.0 l of acetone was added to form a precipitate. The obtained precipitate was filtered, washed with acetone and dried for 24 hours.

The precipitate was dissolved in 200 ml of water and 800 ml of acetone, and stirred for 5 minutes. The precipitate was filtered, dissolved in a mixture of 200 ml of water and 600 ml of acetone, and stirred for 5 minutes. The precipitate was filtered, washed with acetone and vacuum dried for 24 hours.

The reaction product was dissolved in 100 ml of water, and the water insoluble fraction was filtered away. 1.0 l of acetone was added to the filtrate to form a precipitate. The obtained precipitate was filtered and dissolved in a mixture of 50 ml of water and 50 ml of methanol.

The insoluble fraction in the water and methanol mixture was filtered, washed with acetone and vacuum dried for 24 hours.

The dried powder was dissolved in water, the water insoluble fraction of the solution was completely dissolved with an appropriate amount of $H_2SO_4$.5% of THF by volume with respect to the total solution was carefully added to the solution and the acetone was vapor diffused into the solution at room temperature for 12 hours. Then, the reaction product was stored in a refrigerator set at 6° C. for 12 hours to give colorless crystalline cucurbit[7]uril in a yield of 20%.

Method 2

7 ml of formaldehyde was added to 5.68 g of glycoluril and stirred at 70° C. for 30 minutes. 1.0 ml of 12M-HCl aqueous solution was added to the reaction mixture and stirred at 75° C. for 30 minutes. After the reaction was completed, the reaction solution hardened, forming a gel. The obtained gel was washed with water and acetone, and vacuum dried overnight. 10 ml of 11M-$H_2SO_4$ aqueous solution was added to the resultant solid compound and stirred at 80° C. for 12 hours.

The reaction mixture was diluted with 200 ml of water, and 1.0 ml of acetone was further added to form a precipitate. The precipitate was filtered and then stirred in a mixture of 200 ml of water and 600 ml of acetone for 5 minutes. The precipitate was filtered, washed with acetone and vacuum dried for 24 hours.

The product was dissolved in 100 ml of water, and the water insoluble fraction was filtered. 1.0 ml of acetone was added to the filtrate to form a precipitate. The precipitate was filtered with acetone and dissolved in a solution of 50 ml of water and 60 ml of methanol. The insoluble fraction in the water and methanol mixture was filtered, washed with acetone and vacuum dried for 24 hours.

The dried powder was dissolved in water, and an appropriate amount of sulfuric acid was added to dissolve the water insoluble fraction. 5% of THF by volume with respect to the volume of the solution was carefully added to the solution and acetone was vapor diffused into the solution at room temperature for 12 hours. The reaction product was stored in a refrigerator set at 6° C. for 12 hours to give colorless crystalline cucurbit[7]uril in a yield of 20%.

Method 3

5.68 g of glycoluril, 10.0 ml of formaldehyde and 1.0 ml of concentrated HCl were put into a high-pressure reactor, and reacted at 115° C. for 12 hours. After the reaction was completed, a powdered reaction product was obtained. The solid powdered reaction product was washed with water and acetone, and vacuum dried overnight. 10 ml of 10M-$H_2SO_4$ aqueous solution was added to the dried compound, and stirred at 80° C. for 12 hours.

The reaction product was diluted with 200 ml of water, and 1.0 l of acetone was added to the solution to form a precipitate. The precipitate was filtered, 200 ml of water and 800 ml of acetone were added to the precipitate, and stirred for 5 minutes.

The obtained precipitate was filtered, 200 ml of water and 600 ml of acetone were added to the precipitate, and stirred for 5 minutes. The precipitate was filtered, washed with acetone and vacuum dried for 24 hours.

The dried product was dissolved in 100 ml of water and the water insoluble fraction was filtered. 1.0 l of acetone was added to the filtrate to form a precipitate. The precipitate was filtered and dissolved in a mixture of 50 ml of water and 60 ml of methanol.

The insoluble fraction in the water and methanol mixture was filtered, washed with acetone and vacuum dried for 24 hours.

The dried solid powder was dissolved in water and an appropriate amount of $H_2SO_4$ was carefully added to dissolve the water insoluble fraction. 5% of THF by volume with respect to the volume of the solution was carefully added to the solution, and acetone was vacuum diffused into the solution at room temperature for 2 hours. The reaction product was stored in a refrigerator set at 6° C. for 12 hours to give colorless crystalline cucurbit[7]uril in a yield of 20%.

$^1$H NMR ($D_2O/CF_3COOD/D_2SO_4$, 500 MHz), δ4.29 (d, 14H, J=15.5 Hz), 5.60 (s, 14H), 5.91 (d, 14H, J=15.5 Hz)
$^{13}$C NMR ($D_2O/CF_3COOD/D_2SO_4$, 125 MHz), δ56.5, 75.2, 160.2

Figure 4:
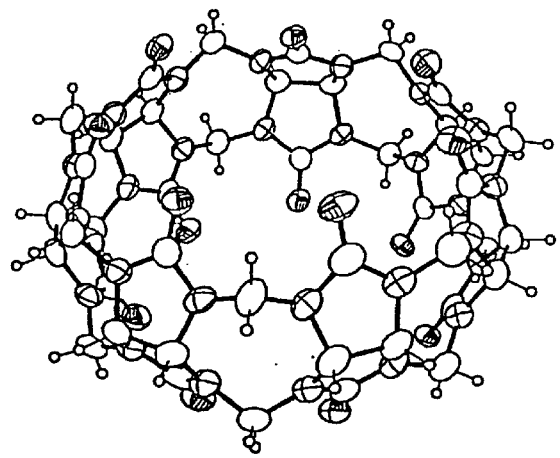

The crystal structure of the obtained cucurbituril derivative was determined by X-ray crystallography. The result is shown in FIG. 4.

Synthesis Example 3

Preparation of the Cucurbituril Derivative Having the Formula (1) where n=8, X=O, $R_1$=H and $R_2$=H Method 1

5.68 g of glycoluril and 20 ml of 9 $M-H_2SO_4$ aqueous solution were put into a reaction flask, and stirred at 70° C. for 30 minutes. Then, 7.0 ml of formaldehyde was added to the reaction mixture and stirred at 75° C. for 24 hours.

The reaction mixture was diluted with 100 ml of water, and stored at 6° C. to room temperature for 12 hours to 3 days to give colorless crystalline cucurbit[8]uril in a yield of 10%.

Method 2

5.68 g of glycoluril and 7.0 ml of formaldehyde were put into a reaction flask, and stirred at 70° C. for 30 minutes. 1.0 ml of HCl was added to the reaction mixture and further stirred at 75° C. for 30 minutes. After the reaction was completed, the reaction solution hardened, forming a gel. The obtained gel was washed with water and acetone, and vacuum dried overnight. 10 ml of $11M-H_2SO_4$ aqueous solution was added to the resultant solid powder and stirred at 80° C. for 12 hours.

The reaction mixture was diluted with 100 ml of water, and stored at room temperature for 12 hours to 3 days to give colorless crystalline cucurbit[8]uril in a yield of 10%.

Method 3

5.68 g of glycoluril, 10.0 mR of formaldehyde and 1.0 ml of HCl were put into a high-pressure reactor, and reacted at 115° C. for 12 hours. After the reaction was completed, a powdered reaction product was obtained. The powdered reaction product was washed with water and acetone, and vacuum dried overnight. 10 ml of $10M-H_2SO_4$ aqueous solution was added to the dried compound, and stirred at 80° C. for 12 hours.

The reaction product was diluted with 150 ml of water, and stored at room temperature for 12 hours to 3 days to give colorless crystalline cucurbit[8]uril in a yield of 10%.

$^1$H NMR ($D_2O/CF_3COOD/D_2SO_4$, 500 MHz), δ4.28 (d, 16H, J=15.5 Hz), 5.60 (s, 14H), 5.91 (d, 16H, J=15.5 Hz)
$^{13}$C NMR ($D_2O/CF_3COOD/D_2SO_4$, 125 MHz), δ57.6, 75.9, 160.5

Figure 5:
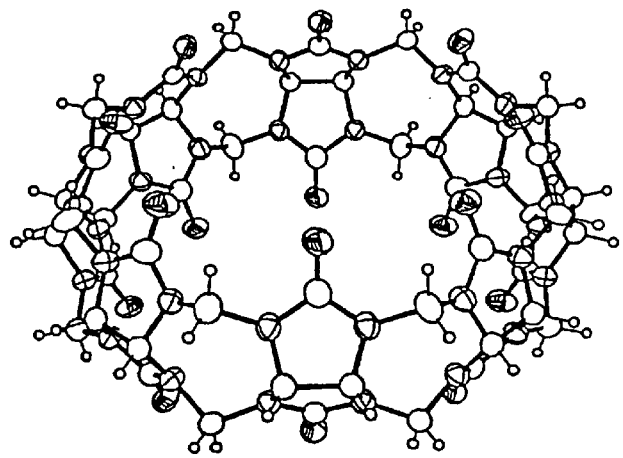

The crystal structure of the obtained cucurbituril derivative was determined by X-ray crystallography. The result is shown in FIG. 5.

Synthesis Example 4

Preparation of the Cucurbituril Derivative Having the Formula (1) where n=6, X=O, $R_1$=H and $R_2$=H Method 1

5.68 g of glycoluril and 20 ml of $9M-H_2SO_4$ aqueous solution were put into a reaction flask, and stirred at 70° C. for 30 minutes. Then, 7.0 ml of formaldehyde was added to the reaction mixture and stirred at 75° C. for 24 hours.

The reaction mixture was diluted with 200 ml of water, and 1.0 l of acetone was added to form a precipitate. The obtained precipitate was filtered, added to 200 ml of water and 800 ml of acetone, and stirred for 5 minutes.

The precipitate was filtered, and added to a mixture of 200 ml of water and 600 ml of acetone, and stirred for 5 minutes. The precipitate was filtered, washed with acetone and vacuum dried for 24 hours.

The reaction product was dissolved in 100 ml of water. The water insoluble fraction was filtered, washed with acetone and vacuum dried for 24 hours to give a colorless solid cucurbit[6]uril in a yield of 50%.

Method 2

5.68 g of glycoluril and 7 ml formaldehyde put into reaction flask, and stirred at 70° C. for 30 minutes. 1.0 ml of HCl was added to the reaction mixture and further stirred at 75° C. for 30 minutes.

After the reaction was completed, the reaction solution hardened, forming a gel. The obtained gel was washed with water and acetone, and vacuum. dried overnight. 10 ml of $11M-H_2SO_4$ aqueous solution was added to the resultant solid compound and stirred at 80° C. for 12 hours.

The reaction mixture was diluted with 200 ml of water, and 1.0 of acetone was further added to form a precipitate. The precipitate was filtered and then stirred in a mixture of 200 ml of water and 600 ml of acetone for 5 minutes.

The precipitate was filtered, added to a mixture of 200 ml of water and 600 ml of acetone, and stirred for 5 minutes. The precipitate was filtered, washed with acetone and vacuum dried for 24 hours.

The dried product was dissolved in water. The water insoluble fraction was filtered and washed with acetone and vacuum dried for 24 hours to give a colorless solid cucurbit[6]uril in a yield of 50%.

Method 3

5.68 g of glycoluril, 8.0 ml of formaldehyde and 1.0 ml of concentrated HCl were put into a high-pressure reactor, and reacted at 115° C. for 12 hours. After the reaction was completed, a powdered reaction product was obtained. The powdered reaction product was washed with water and acetone, and vacuum dried overnight. 10 ml of $10M-H_2SO_4$ aqueous solution was added to the dried compound, and stirred at 80° C. for 12 hours.

The reaction product was diluted with 200 ml of water, and 1.0 l of acetone was added to the solution to form a precipitate. The precipitate was filtered, 200 ml of water and 800 ml of acetone were added to the precipitate, and stirred for 5 minutes.

The obtained precipitate was filtered, 200 ml of water and 600 ml of acetone were added to the precipitate, and stirred for 5 minutes. The precipitate was filtered, washed with acetone and vacuum dried for 24 hours.

The dried product was dissolved in 100 ml of water. The water insoluble fraction was filtered, washed with acetone, and vacuum dried for 24 hours to give a colorless crystalline cucurbit[6]uril in a yield of 50%.

$^1$H NMR ($D_2O/CF_3COOD/D_2SO_4$, 500 MHz), δ4.31 (d, 12H, J=15.5 Hz), 5.59 (s, 12H), 5.87 (d, 12H, J=15.5 Hz)
$^{13}$C NMR ($D_2O/CF_3COOD/D_2SO_4$, 125 MHz), δ55.3, 74.2, 160.0

Synthesis Example 5

Preparation of the Cucurbituril Derivative Having the Formula (1) where n=5 to 20, X=O, $R_1$=H and $R_2$=H Method 1

5.68 g of glycoluril and 20 ml of 9M-$H_2SO_4$ aqueous solution were put into a reaction flask, and stirred at 70° C. for 30 minutes. Then, 7.0 ml of formaldehyde was added to the reaction mixture and stirred at 70 to 75° C. for 24 hours.

Then, the temperature of the reaction mixture was further raised up to 95 to 100° C. and stirred for 12 hours. The reaction product was diluted with 50 ml of water and 1.0 l of acetone was added to form a precipitate. The obtained precipitate was filtered, washed with acetone and dried for 24 hours, to give a mixture of cucurbituril derivatives having the formula (1) hereinabove, where n is a value from 5 to 20. The obtained mixture of cucurbituril derivatives includes 15% of the cucurbituril derivative having n=5, 50% of the cucurbituril derivative having n=6, 20% of the cucurbituril derivative having n=7, 10% of the cucurbituril derivative having n=8, and 5% of the cucurbituril derivative having n=9 through 20.

Method 2

8 ml of formaldehyde was added to 5.68 g of glycoluril and stirred at 75° C. C for 20 minutes. 1.0 ml of 12M-HCl was added to the reaction mixture and stirred at 70 to 75° C. for 30 minutes. After the reaction was completed, the reaction solution hardened, forming a gel. The obtained gel was washed with water and acetone, and vacuum dried overnight.

18 m of 11M-$H_2SO_4$ aqueous solution was added to the resultant solid compound and stirred at 80° C. for 12 hours to give a mixture of cucurbituril derivatives having the formula (1) hereinabove, where n is a value from 5 to 20. The obtained mixture of cucurbituril derivatives includes 15% of the cucurbituril derivative having n=5, 50% of the cucurbituril derivative having n=6, 20% of the cucurbituril derivative having n=7, 10% of the cucurbituril derivative having n=8, and 5% of the cucurbituril derivative having n=9 through 20.

Method 3

5.68 g of glycoluril, 10.0 ml of formaldehyde and 1.0 ml of concentrated HCl were put into a high-pressure reactor, and reacted at 115° C. for 12 hours. After the reaction was completed, a powdered reaction product was obtained. The powdered reaction product was washed with water and acetone, and vacuum dried overnight. 10 ml of 10M-$H_2SO_4$ aqueous solution was added to the dried compound, and stirred at 80° C. for 12 hours, to give a mixture of cucurbituril derivatives having the formula (1) hereinabove, where n is a value from 5 to 20. The obtained mixture of cucurbituril derivatives includes 15% of the cucurbituril derivative having n=5, 50% of the cucurbituril derivative having n=6, 20% of the cucurbituril derivative having n=7, 10% of the cucurbituril derivative having n=8, and 5% of the cucurbituril derivative having n=9 through 20.

By similar methods to Synthesis Examples 1 through 5, the cucurbituril derivatives were obtained having the formula (1) where n=8, X=O, $R_1$ is a methyl group and $R_2$ is hydrogen; n=7, X=O, $R_1$ is a ethyl group and $R_2$ is hydrogen; n=6, X=O, $R_1$ is a propyl group and $R_2$ is hydrogen; n=5, X=O, $R_1$ is a isopropyl group and $R_2$ is hydrogen; n=7, X=O, $R_1$ is a butyl group and $R_2$ is hydrogen; n=6, X=O, $R_1$ is an isobutyl group and $R_2$ is hydrogen; n=5, X=O, $R_1$ is a t-butyl group and $R_2$ is hydrogen; n=6, X=O, $R_1$ is a phenyl group and $R_2$ is hydrogen, n=6, X=O, $R_1$ is a pyridyl group and $R_2$ is hydrogen; n=8, X=O, $R_1$ is hydrogen and $R_2$ is a methyl group; n=6, X=O, $R_1$ is hydrogen and $R_2$ is a propyl group; n=6, X=O, $R_1$ is hydrogen and $R_2$ is a phenyl group; n=6, X=O, $R_1$ is hydrogen and $R_2$ is a trichloromethyl group; n=7, X=O, $R_1$ is hydrogen and $R_2$ is a trichloromethyl group; n=6, X=O, $R_1$ is hydrogen and $R_2$ is a trifluorophenyl group; n=6, X=O, $R_1$ is hydrogen and $R_2$ is α, α, α-trifluorotolyl group; n=6, X=O, $R_1$ is a methyl group and $R_2$ is a methyl group; n=6, X=O, $R_1$ is a methyl group and $R_2$ is a propyl group; n=6, X=O, $R_1$ is a methyl group and $R_2$ is a phenyl group; n=6, X=O, $R_1$ is a methyl group and $R_2$ is a trichloromethyl group; n=6, X=O, $R_1$ is a methyl group and $R_2$ is a trifluoromethyl group; n=6, X=O, $R_1$ is a methyl group and $R_2$ is a parafluorophenyl group; and n=6, X=O, $R_1$ is a methyl group and $R_2$ is α, α, α-trifluorotolyl group.

Synthesis Example 6

Preparation of the Cucurbituril Derivative Having the Formula (1) where n=5, X=S, $R_1$=H and $R_2$=H The objective compound was synthesized with the same methods as those in Synthesis Example 1, except that compund (A) with X=S was used instead of glycoluril.

Synthesis Example 7

Preparation of the Cucurbituril Derivative Having the Formula (1) where n=7, X=S, $R_1$=H and $R_2$=H The objective compound was synthesized with the same methods as those in Synthesis Example 2, except that compound (A) with X=S was used instead of glycoluril.

Synthesis Example 8

Preparation of the Cucurbituril Derivative Having the Formula (1) where n=8, X=S, $R_1$=H and $R_2$=H The objective compound was synthesized with the same methods as those in Synthesis Example 3, except that compund (A) with X=S was used instead of glycoluril.

Synthesis Example 9

Preparation of the Cucurbituril Derivative Having the Formula (1) where n=6, X=S, $R_1$=H and $R_2$=H The objective compound was synthesized with the same methods as those in Synthesis Example 4, except that compound (A) with X=S was used instead of glycoluril.

Synthesis Example 10

Preparation of the Cucurbituril Derivative Having the Formula (1) where n=5 to 20, X=S, $R_1$=H and $R_2$=H The objective compound was synthesized with the same methods as those in Synthesis Example 5, except that compound (A) with X=S was used instead of glycoluril.

The effect of the cucurbituril derivatives obtained in Synthesis Examples 1 through 5 in removing organic dyes has been verified in the following examples.

EXAMPLE 1

30 mg of organic dye, Direct Red 5B (commercially available from Ciba-Geigy Co.) was dissolved in 150 ml of water to prepare an organic dye solution. To half the organic dye solution, 150 mg of cucurbit[7]uril was added and stirred for 30 minutes.

The precipitate was filtered, and UV absorption spectra were measured at $\lambda_{max}$=510 nm on the filtrate and the remaining half of the organic dye solution which was not treated with the cucurbut[7]uril.

As a result, the UV absorption intensity of the untreated solution was 1.43 and that of the solution treated with the curcurbit[7]uril was $2.37 \times 10^{-2}$. The degree of dye removed by the cucurbit[7]uril, which is quantized with R as follows, was 1.7%.

R=UV absorption intensity of the dye solution treated with cucurbit[7]uril x100/UV absorption intensity of the dye solution before the treatment with cucurbit[7]uril The same measurement was carried out with different dyes, and the result of UV absorption spectra is shown in Table 1. The following dyes were used: Reactive Blue HE-G (produced by Kyung-In Co.), Direct Solophenyl Violet 4BL (produced by Ciba-Geigy Co.), Reactive Navy Blue HE-R 150 (produced by Kyung-In Co.), Disperse Yellow E-3 (produced by LG Co.), Disperse T/Q Blue S-GL (produced by LG Co.) and Orange TGL (produced by Ciba-Geigy Co.).

TABLE 1

| Dye | Manufacturer | $\lambda_{max}$ (nm) | Absorption intensity before treatment | Absorption intensity after treatment | R (%) |
|---|---|---|---|---|---|
| Direct Red 5B | Ciba-Geigy Co. | 510 | 1.43 | $2.37 \times 10^{-2}$ | 1.7 |
| Reactive Blue HE-G | Kyung In Co. | 626 | 1.13 | $3.93 \times 10^{-2}$ | 0.3 |
|  |  | 662 | 1.18 | $3.77 \times 10^{-3}$ | 0.3 |
| Direct Solophenyl Violet 4BL | Ciba Geigy Co. | 546 | 0.779 | $9.74 \times 10^{-3}$ | 1.3 |
| Reactive Navy Blue HE-R 150 | Kung In Co. | 609 | 0.262 | $1.57 \times 10^{-3}$ | 0.6 |
| Disperse Yellow E-3 | LG Co. | 429 | 0.774 | $2.33 \times 10^{-2}$ | 3.0 |
| Disperse T/Q Blue S-GL 200 | LG Co. | 776 | 0.386 | $3.25 \times 10^{-3}$ | 0.8 |
| Orange TGL | Ciba Geigy Co. | 419 | 0.161 | $8.69 \times 10^{-3}$ | 5.4 |

EXAMPLE 2

The process of Example 1 was followed, except that a mixture of 80 mg of cucurbit[7]uril and 70 mg of cucurbit[8]ril was used instead of 150 mg of cucurbit[7]uril. In other words, Direct Red 5B (commercially available from Ciba-Geiba Co.) was used as an organic dye, and UV absorption spectra were measured at $\lambda_{max}$=510 nm on the filtrate before and after the treatment with the mixture of the cucurbituril.

As a result, the UV absorption intensity of the untreated solution was 1.43 and that of the solution treated with the mixture of the cucurbituril was $2.02 \times 10^{-2}$. R was 1.4%.

The same measurement was carried out with different dyes, and the result of UV absorption spectra is shown in Table 2.

TABLE 2

| Dye | Manufacturer | $\lambda_{max}$ (nm) | Absorption intensity before treatment | Absorption intensity after treatment | R (%) |
|---|---|---|---|---|---|
| Direct Red 5B | Ciba-Geigy Co. | 510 | 1.43 | $2.02 \times 10^{-2}$ | 1.4 |
| Reactive Blue HE-G | Kyung In Co. | 626 | 1.13 | $3.89 \times 10^{-3}$ | 0.3 |
|  |  | 662 | 1.18 | $3.86 \times 10^{-3}$ | 0.3 |

TABLE 2-continued

| Dye | Manufacturer | $\lambda_{max}$ (nm) | Absorption intensity before treatment | Absorption intensity after treatment | R (%) |
|---|---|---|---|---|---|
| Direct Solophenyl Violet 4BL | Ciba Geigy Co. | 5.46 | 0.779 | $9.11 \times 10^{-3}$ | 1.2 |
| Reactive Navy Blue HE-R 150 | Kung In Co. | 609 | 0.262 | $1.48 \times 10^{-3}$ | 0.6 |
| Disperse Yellow E-3 | LG Co. | 429 | 0.774 | $2.35 \times 10^{-2}$ | 3.0 |
| Disperse T/Q Blue S-GL 200 | LG Co. | 776 | 0.386 | $3.27 \times 10^{-3}$ | 0.8 |
| Orange TGL | Ciba Geigy Co. | 419 | 0.161 | $8.78 \times 10^{-3}$ | 5.5 |

EXAMPLE 3

The process of Example 1 was followed, except that a mixture of cucurbituril derivatives from Synthesis Examples 5, where n is a value from 5 to 20, was used instead of the cucurbit[7]uril. In other words, Direct Red 5B (commercially available from Ciba-Geigy Co.) was used as an organic dye, and UV absorption spectra were measured at $\lambda_{max}$=510 nm on the filtrate before and after the treatment with the mixture of the cucurbituril.

As a result, the UV absorption intensity of the untreated solution was 1.43 and that of the solution treated with the mixture of the cucurbituril was $2.75 \times 10^{-2}$. R was 1.9%.

The same measurement was carried out with different dyes, and the result of UV absorption spectra is shown in Table 3.

TABLE 3

| Dye | Manufacturer | $\lambda_{max}$ (nm) | Absorption intensity before treatment | Absorption intensity after treatment | R (%) |
|---|---|---|---|---|---|
| Direct Red 5B | Ciba-Geigy Co. | 510 | 1.43 | $2.75 \times 10^{-2}$ | 1.9 |
| Reactive Blue | Kyung In Co. | 626 | 1.13 | $3.90 \times 10^{-3}$ | 0.3 |
| HE-G | | 662 | 1.18 | $3.80 \times 10^{-3}$ | 0.3 |
| Direct Solophenyl Violet 4BL | Ciba Geigy Co. | 546 | 0.779 | $9.24 \times 10^{-3}$ | 1.2 |
| Reactive Navy Blue HE-R 150 | Kung In Co. | 609 | 0.262 | $1.31 \times 10^{-3}$ | 0.5 |
| Disperse Yellow E-3 | LG Co. | 429 | 0.774 | $2.18 \times 10^{-2}$ | 2.8 |
| Disperse T/Q Blue S-GL 200 | LG Co. | 776 | 0.386 | $3.47 \times 10^{-3}$ | 0.9 |
| Orange TGL | Ciba Geigy Co. | 419 | 0.161 | $7.22 \times 10^{-3}$ | 4.5 |

The above results of Examples 1 and 2 show that the cucurbituril derivatives obtained in Synthesis Examples 1 through 3 are effective in removing various organic dyes from water.

The result of Example 3 shows that the mixture of cucurbituril derivatives hereinabove, where n is a value from 5 to 20, obtained in Synthesis Example 5, show similar organic dye removal effect to that of separate cucurbituril derivatives produced in Examples 1 through 3. This result supports the fact that the cucurbituril derivatives disclosed by the present invention can be used in the form of a mixture to remove organic dyes without being separated. Thus, the use of the mixture of cucurbituril derivatives can reduce the cost for organic dye removal.

The capabilities of the cucurbituril derivatives obtained in Synthesis Examples 1 through 5 to form stable inclusion complexes with various organic molecules have been verified in the following examples.

EXAMPLE 4

5.80 mg of 2,6-Bis(4,5-dihydro-1H-imidazol-2-yl) naphthalene dihydrochloride and 5.0 mg of cucurbit[8]uril were dissolved in water. NMR spectroscopy confirms quantitative formation of a 1:2 host-guest complex.

$^1$H NMR (D$_2$O, 500 MHz): δ4.21 (d, 16H, J=15.5 Hz), 4.37–4.41 (m, 16H), 5.51 (s, 16H), 5.75 (d, 16H, J=15.5 Hz), 6.91 (d, 4H, J=8.6 Hz), 7.24 (s, 4H), 7.38 (d, 2H, 8.6 Hz)

EXAMPLE 5

120.0 mg of cyclen tetrahydrochloride (1,4,7,10-tetraazacyclodecane tetrahydrochloride) and 100.0 mg of cucurbit[8]uril were dissolved in water. Heating followed by slow cooling of the solution produced an inclusion complex in which a cyclen molecule was encapsulated in the cavity of cucurbit[8]uril as a colorless crystalline material.

$^1$H NMR (D$_2$O, 500 MHz): δ2.67 (s, 16H), 4.33 (d, 16H, J=15.5 Hz), 5.64 (s, 16H), 5.84 (d, 16H, J=15.5 Hz)

EXAMPLE 6

13.0 mg of cyclam tetrahydrochloride (1,4,8,11-tetraazacyclotetradecane tetrahydrochloride) and 10.0 mg of cucurbit[8]uril were dissolved in water. Heating followed by slow cooling of the solution produced an inclusion complex in which a cyclam molecule was encapsulated in the cavity of cucurbit[8]uril as a colorless crystalline material.

$^1$H NMR (D$_2$O, 500 MHz): δ1.76 (m, 4H), 2.41 (s, 8H), 2.63 (m, 8H), 4.30 (d, 16H, J=15.5 Hz), 5.58 (s, 16H), 5.81 (d, 16H, J=15.5 Hz)

EXAMPLE 7

24.2 mg of 1-aminoadanmatane hydrochloride and 50.0 mg of cucurbi[7]uril were dissolved in water. Addition of methanol to the solution produced an inclusion complex in which a 1-aminoadamantane molecule was encapsulated in the cavity of cucurbit[7]uril as a white precipitate.

$^1$H NMR (D$_2$O, 500 MHz): δ1.00 (d, 3H), 1.26 (s, 6H), 1.30 (d, 3H), 1.56 (s, 3H), 4.35 (dd, 14H, J=36.7 Hz), 5.65 (s, 14H), 5.88 (d, 16H, J=15.5 Hz)

EXAMPLE 8

4.35 mg of 2,6-Bis(4,5-dihydro-1H-imidazol-2-yl) naphthalene dihydrochloride and 5.0 mg of cucurbit[7]uril were dissolved in water. NMR spectroscopy confirms quantitative formation of a 1:1 host-guest complex.

$^1$H NMR (D$_2$O, 500 MHz): δ4.21 (d, 14H, J=15.5 Hz), 4.35 (s, 8H), 5.49 (s, 14H), 5.72 (d, 14H, J=15.5 Hz), 6.91 (d, 4H, J=8.6 Hz), 7.24 (d, 2H, J=8.2 Hz), 7.60 (s, 2H), 7.60 (d, 2H, J=8.2 Hz)

The results of Examples 4 through 8 show that the novel cucurbituril derivatives obtained in Synthesis Examples 1 through 5 can be used in extraction, separation and purification of the organic molecules used in the examples, and other organic molecules such as fullerene.

On the other hand, the cucurbituril derivatives obtained in Synthesis Examples 1 through 5 have Lewis base atoms near the cavities of the molecule, and thus they can effectively form a complex with positively charged metal ions or other organic ions. The following example is for investigating whether the cucurbituril derivatives having this property can be applied in manufacturing sensors for sensing positive metal ions or ammonium ions.

EXAMPLE 9

Distilled water and formic acid were mixed in a ratio of 1:1: by volume. Next, 1.0 mM of cucurbit[5]uril derivative was prepared with the diluted formic acid. 20.0 mM of aqueous solution containing ammonium ions, and positive ions of alkaline metals, such as lithium, sodium and potassium, was prepared. Then, the binding constants of the cucurbit[5]uril derivative with these ions were measured using a microcalorimeter (VP-ITC, manufactured by MicroCal). As a result, the cucurbit[5]uril derivative has a binding constant of $5.4 \times 10^3 M^{-1}$ with ammonium ions, $3.3 \times 10^2 M^{-1}$ with positive lithium ions, $4.5 \times 10^3 M^{-1}$ with positive sodium ions, and $2.6 \times 10^4 M^{-1}$ with positive potassium ions. The cucurbit[5]uril derivative can selectively bind with alkali metal ions, as well as with ammonium ions. The result confirms that cucurbituril derivatives can be used as ion sensors.

The following example is for investigating the function of the cucurbituril derivatives obtained in Synthesis Examples 1 through 10, as a drug carrier. In the following example, cisplatin, an anti-cancer drug, was used.

EXAMPLE 10

2.0 mg of Cis-dichloroethylenediamine platinum (II) and 2.0 mg of cucurbit[8]uril were dissolved in water. NMR spectroscopy confirms quantitative formation of a 2:1 complex of the dichloroethylenediamine platinum (II) and cucurbit[8]uril.

$^1$H NMR (D$_2$O, 500 MHz): δ2.63 (m, 16H), 4.26–4.29 (m, 16H), 5.56–5.65 (m, 16H), 5.81–5.87 (m,16H)

The following examples are for investigating whether the cucurbituril derivatives obtained in Synthesis Examples 1 through 5 enables to effectively sense amino acids and the bases of nucleic acids.

EXAMPLE 11

5.0 mM of methylviologendichloride solution, and 5.0 mM of tyrosine solution were prepared using D$_2$O solvent. 0.25 ml of each solution was mixed with 2.1 mg of cucurbit[8]uril. Next, the mixture was heated until the color changed into yellow. NMR spectroscopy conforms quantitative formation of a 1:1:1 complex of methylviolgen, tyrosine and cucurbit[8]uril.

$^1$H NMR (D$_2$O, 500 MHz): δ2.84 (broad m, 2H), 4.10 (broad t, 1H), 4.29 (d, 16H, J=15.5 Hz), 4.63 (s, 6H), 5.59 (s, 16H), 5.83 (d, 16H, J=15.5 Hz), 6.22 (broad s, 2H), 6.77 (broad d, 2H), 7.37 (broad d, 4H), 8.84 (d, 4H, J=6.0 Hz)

EXAMPLE 12

5.0 mM of methylviologendichloride solution, and 5.0 mM of tryptophan solution were prepared using D$_2$O solvent. 0.25 ml of each solution was mixed with 2.1 mg of cucurbit[8]uril. Next, the mixture was heated until the color changed into red. NMR spectroscopy conforms quantitative formation of a 1:1:1 complex of methylviolgen, tryptophan and cucurbit[8]uril.

$^1$H NMR (D$_2$O, 500 MHz): δ3.30 (broad m, 2H), 4.28 (d, 16H, J=15.5 Hz), 4.57 (s, 6H), 5.57 (s, 16H), 5.81 (d, 16H, J=15.5 Hz), 6.16 (broad s, 1H), 6.22 (broad s, 1H), 6.40 (broad s, 1H), 6.82 (broad s, 1H), 7.01 (broad s, 4H), 7.21 (broad s, 1H), 8.64 (broad s, 4H)

EXAMPLE 13

5.0 mM of methylviologendichloride solution, and 5.0 mM of thymine solution were prepared using D$_2$O solvent. 0.25 ml of each solution was mixed with 2.1 mg of cucurbit[8]uril. Next, the mixture was heated until the color changed into yellow. NMR spectroscopy conforms quantitative formation of a 1:1:1 complex of methylviolgen, thymine and cucurbit[8]uril.

$^1$H NMR (D$_2$O, 500 MHz): δ1.67 (s, 3H), 4.24 (d, 16H, J=15.5 Hz), 4.55 (s, 6H), 5.55 (s, 16H), 5.77 (d, 16H, J=15.5 Hz), 7.19 (s, 1H), 7.55 (broad s, 4H), 8.76 (broad s, 4H)

The results from Examples 11 through 13 show that the cucurbituril derivatives obtained in Synthesis Examples 1 through 5 can selectively detect amino acids, which have aromatic side chains, and the base of a particular nucleic acid, such as thymine, and thus the cucurbituril derivatives are applicable in separating such substances, or developing sensors for detecting such substances.

The following example is for investigating whether the cucurbituril derivatives obtained in Synthesis Examples 1 through 5 can be used as additives to pesticides, herbicides, aromatics and the like.

EXAMPLE 14

Methylviologendichloride (so-called paraquat), a herbicide, was used. 5.0 mM of mehylbiologendichloride solution was prepared with D$_2$O solvent. Next, cucurbit[8] uril was added to the solution. NMR spectroscopy conforms quantitative formation of a 1:1 complex of methylviolgen and cucurbit[8]uril.

$^1$H NMR (D$_2$O, 500 MHz): δ4.24 (d, 16H, J=15.5 Hz), 4.74 (s, 6H), 5.55 (s, 16H), 5.78 (d, 16H, J=15.5 Hz), 7.68 (broad, 4H), 8.78 (broad, 4H)

The result from Example 14 shows that the cucurbituril derivatives according to the present invention can release slowly pesticides, herbicides and aromatics captured therein, and thus they can be used as additives in manufacturing pesticides, herbicides, cosmetics, artificially scented papers or textiles.

As previously described, the cucurbituril derivatives having the formula (1) disclosed by the present invention, where X=O, are soluble in water at a neutral pH in the presence of ammonium salts or alkali metal ions, and precipitate together with organic dyes at a certain pH. Also, when in the formula (1) X is S or NH, or $R_1$ or $R_2$ is propyl or longer alkyl chain, the cucurbituril derivatives are soluble in organic solvents, providing wider applications than previously known cucurbituril derivatives. Also, the cucurbituril derivatives disclosed by this invention can encapsulate various compounds with different sizes, Furthermore, they have Lewis base atoms near the entrances to their cavities which allow the cucurbituril derivatives to form complexes with metal ions, organometallic ions or positively charged organic compounds. With these features, the cucurbituril derivatives disclosed by the present invention have wide applications. In addition, the preparation of the cucurbituril derivatives disclosed by the present invention is easily scaled up for industrial purposes. In the cucurbituril derivative preparation according to the present invention, each cucurbituril derivative can be separated from the mixture containing the cucurbituril derivatives having the formula (1), where n is a value from 5 to 20, and a mixture of two or more of the cucurbituril derivatives can also be obtained.

The cucurbituril derivatives and the mixture thereof disclosed by the present invention are applied to remove organic dyes from waste water, heavy metal from water and radioactive isotopes from radioactive wastes, to capture and remove unpleasant odor, and air pollutants such as carbon monoxide, carbon dioxide, $NO_x$ and $SO_x$, and to deodorize and decolorize livestock waste water and ironwork waste water. Also, the cucurbituril derivatives disclosed by the present invention are applicable in manufacturing sensors for sensing ammonium ions, organic amines, amino acid derivatives, nucleic acid bases, alkali metal or alkaline earth metal ions. The cucurbituril derivatives can be used as additives to polymers, cosmetics, artificially scented papers or textiles, pesticides and herbicides, and drugs, and used as drug carriers. The cucurbituril derivatives having the formula (1) can be used for extraction and purification of fullerene or caborane compounds, and used as packing materials of chromatographic columns, as additives to gas separation membranes, as catalysts for various chemical reactions.

In addition, use of the mixture of cucurbituril derivatives prepared by one of the three methods shown in FIG. 1 without separation is advantageous in terms of cost, and can be readily adapted for industrial uses.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A method for preparing cucurbituril derivatives having the formula (1)

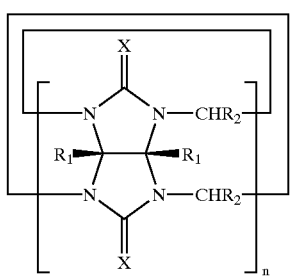

(1)

where X is O, S or NH; $R_1$ and $R_2$ are independently selected from the group consisting of hydrogen, alkyl groups of 1 to 30 carbon atoms, alkenyl groups of 2 to 30 carbon atoms alkynyl groups of 2 to 30 carbon atoms, alkylthio groups of 1 to 30 carbon atoms, alkylcarboyl groups of 2 to 30 carbon atoms, alkoxy group of 1 to 30 atoms haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms unsubstituted aryl groups of 6 to 30 carbon atoms, and aryl groups of 6 to 30 carbon atoms with hetero atoms; and n is an integer from 4 to 20, the method comprising (a1) adding 3 to 7 moles of an acid to 1 mole of compound (A) having the formula (A) to form a mixture, adding 2 to 20 moles of an aldehyde of formula (B) to the mixture, and stirring the mixture at 70 to 95° C.; and

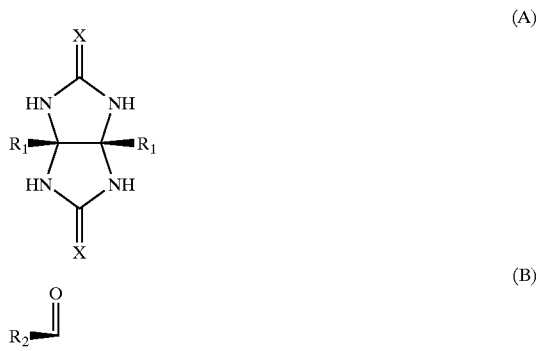

(b1) stirring the reaction product at 95 to 105° C. to complete the reaction.

2. The method of claim 1, wherein the reaction product of step (b1) is a mixture of two or more cucurbituril derivatives having the formula (1) where n is a value from 5 to 20.

3. The method of claim 1, wherein the reaction product of step (b1) is a mixture of 5–30% of the cucurbituril derivative having n=5, 30–70% of the cucurbituril derivative having n=6, 5–30% of the cucurbituril derivative having n=7, 2–15% of the cucurbituril derivative having n=8, and 1–10% of the cucurbituril derivative having n=9 to 20.

4. The method of claim 1, further comprising the steps of:

(c1) recrystallizing the reaction product of step (b1) with water to obtain the cucurbituril derivative having the formula (1) with n=8;

(d1) diluting the remaining solution after step (c1) with water and acetone to produce a precipitate which is filtered and further treated in step (e1), and removing the solvent from the resulting filtrate to obtain the cucurbituril derivatives having the formula (1), where n is a value from 9 to 20; and (e1) partially dissolving the precipitate obtained in step (d1) in water to obtain the cucurbituril derivatives with n=5 and 7 from the water soluble fraction, and the cucurbituril derivative with n=6 from the water insoluble fraction.

5. The method of claim 4, wherein the water soluble fraction containing the cucurbituril derivatives with n=5 and 7, obtained in step (e1), is separated into the cucurbituril derivative having the formula (1) where n=5, and the cucurbituril derivative having the formula (1) where n=7, with a mixture of water and methanol.

6. The method of claim 1, wherein the acid used in step (a1) is at least one selected from the group consisting of hydrochloric acid, sulfuric acid, phosphoric acid, acetic acid and nitric acid, and the acid is diluted with water or an organic in a concentration of 1 to 12M.

7. A method for preparing cucurbituril derivatives having the formula (1)

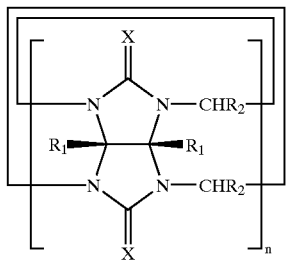

(1)

where X is O, S or NH; $R_1$ and $R_2$ are independently selected from the group consisting of hydrogen, alkyl groups of 1 to 30 carbon atoms, alkenyl groups of 2 to 30 carbon atoms alkynyl groups of 2 to 30 carbon atoms, alkylthio groups of 1 to 30 carbon atoms, alkylcarboxyl groups of 2 to 30 atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n is an integer from 4 to 20, the method comprising:

(a2) adding 0.1 to 1 moles of an acid to 1 mole of compound (A) having the formula (A) to form a mixture, adding 2 to 20 moles of an aldehyde of formula (B) to the mixture, and stirring the mixture at 70 to 85° C., to obtain an intermediate in a gel state; and

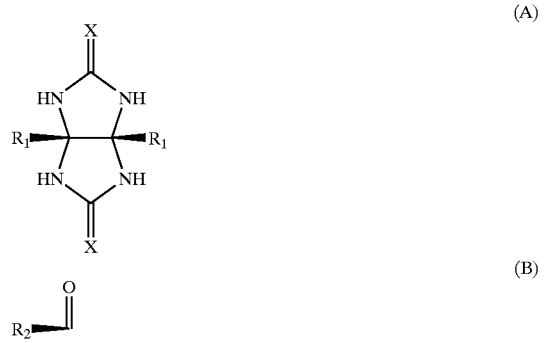

(b2) drying the intermediate in a gel state, adding 3 to 7 moles of an acid with respect to 1 mole of the dried intermediate, and stirring the reaction product at 70 to 105° C.

8. The method of claim 7, wherein the reaction product of step (b2) is a mixture of two or more cucurbituril derivatives having the formula (1) where n is a value from 5 to 20.

9. The method of claim 7, wherein the reaction product of step (b2) is a mixture of 5–30% of the cucurbituril derivative having n=5, 30–70% of the cucurbituril derivative having n=6, 5–30% of the cucurbituril derivative having n=7, 2–15% of the cucurbituril derivative having n=8, and 1–10% of the cucurbituril derivative having n=9 to 20.

10. The method of claim 7, further comprising the steps of:

(c2) recrystallizing the reaction product of step (b2) with water and acetone to obtain the cucurbituril derivative having the formula (1) with n=8;

(d2) diluting the remaining solution after step (c2) with water and acetone to produce a precipitate which is filtered and further treated in step (e2), and removing the solvent from the resulting filtrate to obtain the cucurbituril derivatives having the formula (1), where n is a value from 9 to 20; and (e2) partially dissolving the precipitate obtained in step (d2) in water to obtain the cucurbituril derivatives with n=5 and 7 from the water soluble fraction, and the cucurbituril derivative with n=6 from the water insoluble fraction.

11. The method of claim 10, wherein the water soluble fraction containing the cucurbituril derivatives with n=5 and 7, obtained in step (e2), is separated into the cucurbituril derivative having the formula (1) where n=5, and the cucurbituril derivative having the formula (1) where n=7, with a mixture of water and methanol.

12. The method of claim 7, wherein the acid used in step (a2) is at least one selected from the group consisting of hydrochloric acid, sulfuric acid, phosphoric acid, acetic acid and nitric acid, and the acid is diluted with water or an organic solvent in a concentration of 1 to 12M.

13. A method for preparing cucurbituril derivatives having the formula (1)

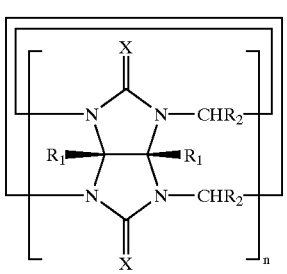

(1)

where X is O, S or NH; $R_1$ and $R_2$ are independently selected from the group consisting of hydrogen, alkyl groups of 1 to 30 carbon atoms, alkenyl groups of 2 to 30 carbon atoms, alkynyl groups of 2 to 30 carbon atoms, alkylthio groups of 1 to 30 carbon atoms, alkylcarboxyl groups of 2 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n is an integer from 4 to 20, the method comprising:

(a3) putting compound (A), and 0.1 to 1 moles of an acid and 2 to 20 moles of an aldehyde of formula (B) with respect to 1 mole of compound (A), in a high-pressure reactor, reacting the mixture at 80 to 130° C., to obtain oligomers in powder form; and

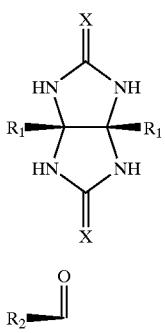

(b3) adding 3 to 7 moles of an acid with respect to 1 mole of the oligomers, and stirring the mixture at 70 to 105° C.

14. The method of claim 13, wherein the reaction product of step (b3) is a mixture of two or more cucurbituril derivatives having the formula (1) where n is a value from 5 to 20.

15. The method of claim 13, wherein the reaction product of step (b3) is a mixture of 5–30% of the cucurbituril derivative having n=5, 30–70% of the cucurbituril derivative having n=6, 5–30% of the cucurbituril derivative having n=7, 2–15% of the cucurbituril derivative having n=8, and 1–10% of the cucurbituril derivative having n=9 to 20.

16. The method of claim 13, further comprising the steps of:

(c3) recrystallizing the reaction product of step (b3) with water and acetone to obtain the cucurbituril derivative having the formula (1) with n=8;

(d3) diluting the remaining solution after step (c3) with water and acetone to produce a precipitate which is filtered and further treated in step (e3), and removing the solvent from the resulting filtrate to obtain the cucurbituril derivatives having the formula (1), where n is a value from 9 to 20; and (e3) partially dissolving the precipitate obtained in step (d3) in water to obtain the cucurbituril derivatives with n=5 and 7 from the water soluble fraction, and the cucurbituril derivative with n=6 from the water in soluble fraction.

17. The method of claim 16, wherein the water soluble fraction containing the cucurbituril derivatives with n=5 and 7, obtained in step (e3), is separated into the cucurbituril derivative having the formula (1) where n=5, and the cucurbituril derivative having the formula (1) where n=7, with a mixture of water and methanol.

18. The method of claim 13, wherein, in step (a3), the pressure of the high-pressure reactor is in the range of 15 to 100 psi.

19. The method of claim 13, wherein the acid used in the steps (a3) and (b3) is at least one selected from the group consisting of hydrochloric acid, sulfuric acid, phosphoric acid, acetic acid and nitric acid, and the acid is diluted with water or an organic solvent in a concentration of 1 to 12M.

* * * * *